United States Patent
Inoue et al.

(10) Patent No.: US 10,920,234 B2
(45) Date of Patent: Feb. 16, 2021

(54) **METHOD OF PRODUCING TRANSGENIC *TARAXACUM* PLANT**

(71) Applicant: SUMITOMO RUBBER INDUSTRIES, LTD., Kobe (JP)

(72) Inventors: Yukino Inoue, Kobe (JP); Haruhiko Yamaguchi, Kobe (JP); Teruhiko Terakawa, Yokohama (JP); Tsubasa Yano, Yokohama (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

(21) Appl. No.: 16/435,010

(22) Filed: Jun. 7, 2019

(65) Prior Publication Data

US 2020/0010837 A1   Jan. 9, 2020

(30) Foreign Application Priority Data

Jul. 5, 2018  (JP) ............................. JP2018-128251

(51) Int. Cl.
 *C12N 15/82* (2006.01)
(52) U.S. Cl.
 CPC ................ *C12N 15/8205* (2013.01)
(58) Field of Classification Search
 CPC ................................................ C12N 15/8205
 USPC ...................................................... 800/294
 See application file for complete search history.

(56) References Cited

U.S. PATENT DOCUMENTS

| 7,026,529 | B2 * | 4/2006 | Ryu et al. | ............. | C12N 15/82 800/294 |
| 2005/0022267 | A1 | 1/2005 | Ryu et al. | | |

OTHER PUBLICATIONS

Lotta Oscarsson Production of rubber from dandelion-a proof of concept for a new method of cultivation Master thesis. Jan. 28, 2015.*

Bae et al. Agrobacterium tumefaciens-mediated transformation of a medecinal plant *Taraxacum playtycarpum*. Plant Cell Tissue and Organ Culture (2005) 80 51-57.*

Abdur Rashid Comparison of a kanamycin versus hygromycin resistance gene in transgenic plant selection of *Arabidopsis thaliana* L. Adv. Cell Sci. Tissue Cul. 2017;1(1):1-2.*

Martins et al. A Simple and Highly Efficient Agrobacterium-Mediated Transformation Protocol for Seteria Viridis biotchnology Reports 6 (2015) 41-44.*

Pereira et al. Optimal Concentration of selective agents for inhibiting in vitro growth of Urochloa brizantha embryogenic calli. African Journal of Biotechnology Apr. 8, 2016.*

Post et al., "Laticifer-Specific cis-Prenyltransferase Silencing Affects the Rubber, Triterpene, and Inulin Content of Taraxacum brevicorniculatum1,2[C][W]", Plant Physiology, vol. 158, Mar. 2012, 1406-1417 (15 pages total).

Stolze et al., "Development of rubber-enriched dandelion varieties by metabolic engineering of the inulin pathway", Plant Biotechnology Journal, vol. 15, 2017, pp. 740-753.

Zhang et al., "Rapid and hormone-free Agrobacterium rhizogenes-mediated transformation in rubber producing dandelions *Taraxacum kok-saghyz* and *T. brevicorniculatum*", Industrial Crops and Products, vol. 66, 2015, pp. 110-118 (10 pages).

* cited by examiner

*Primary Examiner* — Annette H Para
(74) *Attorney, Agent, or Firm* — Birch, Stewart, Kolasch & Birch, LLP

(57) ABSTRACT

Provided is a method that can efficiently produce a transgenic *Taraxacum* plant in a short period. A method of producing a transgenic *Taraxacum* plant, including: an infection step of infecting a tissue fragment from a *Taraxacum* plant with an *Agrobacterium tumefaciens* containing a plasmid containing a target gene or fragment thereof and hygromycin-resistance gene; a selective culture step of selecting the tissue fragment that has acquired the target gene from the tissue fragment obtained in the infection step by using hygromycin; a callus-inducing step of culturing the tissue fragment obtained in the selective culture step in a callus-inducing medium to form callus; a regeneration-inducing step of culturing the callus obtained in the callus-inducing step in a regeneration-inducing medium to form an adventitious embryo, an adventitious bud, and a shoot; and a rooting step of culturing the shoot obtained in the regeneration-inducing step in a rooting medium to root the shoot.

7 Claims, 2 Drawing Sheets
Specification includes a Sequence Listing.

M : Marker (φX174 DNA-Hae III Digest)
1 : Example 1

```
                        SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic: PRIMER-1

<400> SEQUENCE: 1
gctgatcccc atgtgtatca ctggc                                    25

<210> SEQ ID NO 2
<211> LENGTH: 26
<212> TYPE: DNA
<213> ORGANISM: Artificial Sequence
<220> FEATURE:
<223> OTHER INFORMATION: Synthetic: PRIMER-2

<400> SEQUENCE: 2 ctattcctttt gccctcggac gagtgc                                  26
```

METHOD OF PRODUCING TRANSGENIC *TARAXACUM* PLANT

REFERENCE TO SEQUENCE LISTING SUBMITTED VIA EFS-WEB

This application includes an electronically submitted sequence listing in .txt format. The .txt file contains a sequence listing entitled "5051-0527PUS1 ST25.txt" created on Aug. 27, 2019 and is 714 bytes in size. The sequence listing contained in this .txt file is part of the specification and is hereby incorporated by reference herein in its entirety.

TECHNICAL FIELD

The present invention relates to a method of producing a transgenic *Taraxacum* plant.

BACKGROUND ART

At the present time, natural rubber (a type of polyisoprenoid) for use in industrial rubber products may be obtained by cultivating para rubber tree (*Hevea brasiliensis*) of the family Euphorbiaceae whose laticifer cells biosynthesize natural rubber, and manually harvesting the natural rubber from the plant.

The natural rubber for industrial applications is at present sourced almost entirely from *Hevea brasiliensis*. Moreover, the natural rubber is used widely and in large amounts in a variety of applications as the main raw material for rubber products. However, *Hevea brasiliensis* is a plant that can grow in limited regions such as Southeast Asia and South America. Furthermore, *Hevea brasiliensis* requires about seven years from planting to becoming mature enough for rubber extraction, and the collection season is limited in some cases. The time period during which natural rubber can be collected from the mature tree is also limited to 20 to 30 years.

Demand for natural rubber is expected to grow in the future, especially in developing countries, but for the reasons discussed above it is difficult to greatly increase natural rubber production from *Hevea brasiliensis*. There is therefore concern that natural rubber sources will dry up, and a need exists for a stable source of supply of natural rubber other than mature *Hevea brasiliensis* trees.

In this context, the search for supply sources of natural rubber other than *Hevea brasiliensis* has been actively pursued. It is known that there are at least 2000 species of plants other than *Hevea brasiliensis* that can produce isoprenoids.

If these plants are used as new supply sources of natural rubber, mass propagation of these plants is expected to be required in order to mass produce natural rubber. Mass propagation of plants may be carried out, for example, by cultivating plants from seeds or growing plants from cuttings. These methods, however, are easily influenced by climate, season, or other factors and thus may fail to stably propagate plants.

Meanwhile, there have been attempts to increase production of natural rubber from *Hevea brasiliensis*. Plantlets of *Hevea brasiliensis* may be propagated by raising seedlings from seeds, preparing stocks from the grown seedlings, and then grafting buds obtained from clone seedlings onto the stocks. However, since the buds that can be obtained from clone seedlings are limited, it is necessary to mass propagate superior clone seedlings to spread superior varieties.

Moreover, grafts (conventional clonal propagation techniques) may simultaneously inherit diseases of the original trees, and diseased plantlets may be propagated. Therefore, there is a need for a method capable of stably propagating plants.

Possible methods for increasing the yield of isoprenoids in plants include, for example, modifying plants so as to improve stress resistance or to increase the amount of isoprenoids accumulated in the plants. Modification of plants can be carried out using artificial crossing or mutations, but these methods have difficulty in efficiently imparting desired characteristics and thus are unlikely to be feasible. Therefore, it is considered that modification of plants will be performed using a cellular engineering approach in which a target gene is introduced into plant cells to impart desired characteristics.

Conventional *Agrobacterium*-based transformation methods include forming hairy roots by *Agrobacterium rhizogenes*, and forming adventitious buds from the hairy roots to produce plants. There has been reported a method for transforming dandelion using *Agrobacterium rhizogenes* (see, for example, Non-Patent Literature 1).

CITATION LIST

Non Patent Literature

Non-Patent Literature 1: Yingxiao Zhang and 4 others, "Industrial Crops and Products", 2015, vol. 66, pp. 110-118

SUMMARY OF INVENTION

Technical Problem

As noted above, it has been proposed to transform dandelion using *Agrobacterium rhizogenes*, but this method has a drawback in that the use of *Agrobacterium rhizogenes* simultaneously involves the incorporation of the Ri plasmid which may cause malformation of the transgenic plants. Thus, the conventional transformation methods leave room for improvement, and there has been a need for a method for efficiently transforming *Taraxacum* plants.

The present invention aims to solve the problems and provide a method that can efficiently produce a transgenic *Taraxacum* plant in a short period of time.

Solution to Problem

As a result of extensive research and experimentation, the present inventors successfully produced a transgenic *Taraxacum* plant. The inventors then conducted studies on the conditions for more efficiently producing a transgenic *Taraxacum* plant and found that a transgenic plant can be efficiently produced in a short period of time by using *Agrobacterium tumefaciens* as the *Agrobacterium* to avoid incorporation of any Ri plasmid, and further by adding a specific plant hormone to efficiently induce callus and form an adventitious bud. It was also found that by using hygromycin as a selective reagent, it is possible to efficiently screen recombinants. Based on these findings, the inventors have arrived at the present invention.

Specifically, the present invention relates to a method of producing a transgenic *Taraxacum* plant, including:

an infection step of infecting a tissue fragment from a *Taraxacum* plant with an *Agrobacterium tumefaciens* containing a plasmid containing a target gene or a fragment thereof and a hygromycin-resistance gene;

a selective culture step of selecting the tissue fragment that has acquired the target gene from the tissue fragment obtained in the infection step by using hygromycin;

a callus-inducing step of culturing the tissue fragment obtained in the selective culture step in a callus-inducing medium containing a cytokinin plant hormone, an auxin plant hormone, and a carbon source to form callus;

a regeneration-inducing step of culturing the callus obtained in the callus-inducing step in a regeneration-inducing medium containing a plant growth hormone and a carbon source to form an adventitious embryo, an adventitious bud, and a shoot; and a rooting step of culturing the shoot obtained in the regeneration-inducing step in a rooting medium to root the shoot.

Preferably, the selective culture step includes culturing the tissue fragment obtained in the infection step in a selective culture medium containing 0.1 to 2 mg/L of hygromycin to select the tissue fragment that has acquired the target gene.

Preferably, the callus-inducing medium contains the cytokinin plant hormone at a concentration of 0.5 to 1.2 mg/L and the auxin plant hormone at a concentration of lower than 1.2 mg/L.

Preferably, the plant growth hormone in the regeneration-inducing medium contains a cytokinin plant hormone at a concentration of 0.4 to 1.1 mg/L and an auxin plant hormone at a concentration of lower than 0.2 mg/L.

Preferably, the *Taraxacum* plant is *Taraxacum kok-saghyz* or *Taraxacum brevicorniculatum*.

Advantageous Effects of Invention

The method of producing a transgenic *Taraxacum* plant according to the present invention includes an infection step of infecting a tissue fragment from a *Taraxacum* plant with an *Agrobacterium tumefaciens* containing a plasmid containing a target gene or a fragment thereof and a hygromycin-resistance gene; a selective culture step of selecting the tissue fragment that has acquired the target gene from the tissue fragment obtained in the infection step by using hygromycin; a callus-inducing step of culturing the tissue fragment obtained in the selective culture step in a callus-inducing medium containing a cytokinin plant hormone, an auxin plant hormone, and a carbon source to form callus; a regeneration-inducing step of culturing the callus obtained in the callus-inducing step in a regeneration-inducing medium containing a plant growth hormone and a carbon source to form an adventitious embryo, an adventitious bud, and a shoot; and a rooting step of culturing the shoot obtained in the regeneration-inducing step in a rooting medium to root the shoot. Thus, it is possible to efficiently produce a transgenic *Taraxacum* plant in a short period of time.

DESCRIPTION OF EMBODIMENTS

Figure 1A:
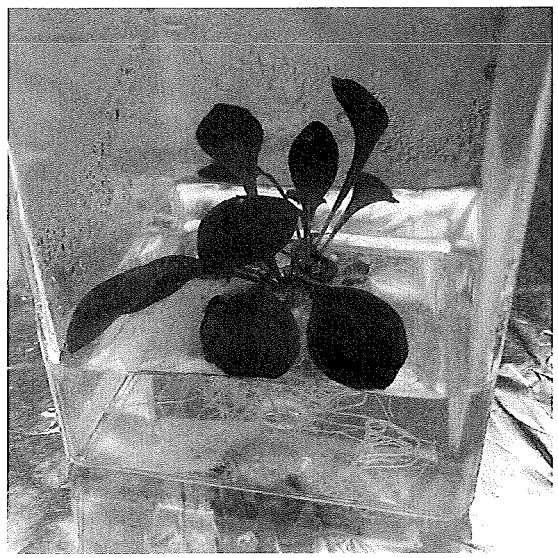
FIGS. 1A and 1B are photographs showing the appearance of the regenerated plants obtained in Example 1.

The production method of the present invention includes an infection step of infecting a tissue fragment from a *Taraxacum* plant with an *Agrobacterium tumefaciens* containing a plasmid containing a target gene or a fragment thereof and a hygromycin-resistance gene; a selective culture step of selecting the tissue fragment that has acquired the target gene from the tissue fragment obtained in the infection step by using hygromycin; a callus-inducing step of culturing the tissue fragment obtained in the selective culture step in a callus-inducing medium containing a cytokinin plant hormone, an auxin plant hormone, and a carbon source to form callus; a regeneration-inducing step of culturing the callus obtained in the callus-inducing step in a regeneration-inducing medium containing a plant growth hormone and a carbon source to form an adventitious embryo, an adventitious bud, and a shoot; and a rooting step of culturing the shoot obtained in the regeneration-inducing step in a rooting medium to root the shoot.

The production method of the present invention may include other steps as long as it includes the aforementioned steps. Each of the aforementioned steps may be performed once or may be carried out a plurality of times by, for example, subculture.

In the present invention, the term "callus" refers to undifferentiated plant cells or an undifferentiated plant cell cluster. As used herein, the term "adventitious embryo" refers to an embryo-like tissue induced from callus, and the term "adventitious bud" refers to a bud-like tissue produced at sites where buds do not usually arise, such as leaves, roots, and internodes of stems. As used herein, the term "shoot" refers to a leaf or a plantlet.

Non-limiting examples of the *Taraxacum* plant include dandelion (*Taraxacum*), *Taraxacum venustum* H. Koidz, *Taraxacum hondoense* Nakai, *Taraxacum platycarpum* Dahlst, *Taraxacum japonicum*, *Taraxacum officinale* Weber, *Taraxacum kok-saghyz*, and *Taraxacum brevicorniculatum*. Among these, the *Taraxacum* plant is preferably *Taraxacum kok-saghyz* or *Taraxacum brevicorniculatum*.

Now, the steps in the production method of the present invention will be described.

<*Agrobacterium tumefaciens* Preparation Step>

The method of the present invention includes infecting a tissue fragment from a *Taraxacum* plant with an *Agrobacterium tumefaciens* containing a plasmid containing a target gene or a fragment thereof and a hygromycin-resistance gene (hereinafter also referred to collectively as "target gene and the like"). Thus, we first explain how to prepare the *Agrobacterium tumefaciens* (*Agrobacterium tumefaciens* preparation step).

The use of *Agrobacterium tumefaciens* provides good infection efficiency without incorporating any Ri plasmid.

The *Agrobacterium tumefaciens* containing a plasmid containing a target gene and the like may be prepared by any conventional method, such as by incorporating a target gene and the like into a plasmid capable of homologous recombination with the T-DNA region of the Ti plasmid of *Agrobacterium tumefaciens* to prepare a target gene recombinant intermediate vector, and introducing the target gene recombinant intermediate vector into *Agrobacterium tumefaciens*. Alternatively, it may be prepared by incorporating a target gene and the like into a binary vector, which is generally used in *Agrobacterium* techniques, to prepare a target gene binary vector, and introducing the vector into *Agrobacterium tumefaciens*. Another method includes introducing a plasmid containing a target gene and the like into *Agrobacterium tumefaciens* by electroporation.

As used herein, the term "target gene" refers to a gene that is intended to be introduced into a *Taraxacum* plant. The target gene may be any gene that can be introduced into a

*Taraxacum* plant so that the genetic trait of the *Taraxacum* plant can be modified. It may be a gene originally possessed by the *Taraxacum* plant into which it is to be introduced, or a gene derived from an organism other than the *Taraxacum* plant, or an artificially constructed gene. The artificially constructed gene may be, for example, a chimeric gene in which two or more genes are linked, or a mutant gene produced by mutation of a gene of any organism. The mutant gene may be produced, for example, by partial deletion or substitution of the bases in the DNA nucleotide sequence of the gene, or by insertion of a partial nucleotide sequence within the nucleotide sequence.

The target gene may also be a structural gene or a regulatory region. For example, it may be a structural gene that contains a transcription or translation control region, e.g. a promoter or terminator. It goes without saying that the control region gene may be any gene that can function in the *Taraxacum* plant into which the gene is to be introduced, and may be a gene derived from an organism of the same species as the *Taraxacum* plant into which the gene is to be introduced or a gene derived from an organism of a different species. Examples of such heterologous promoters include promoters generally used in fields related to genetic transformation, such as CaMV35 promoter and NOS promoter.

The target gene to be introduced into the *Taraxacum* plant may be a full-length gene or a fragment thereof. For example, a fragment consisting only of a functional domain of a structural gene may be introduced.

The target gene to be introduced into the *Taraxacum* plant is preferably, for example, a gene that is involved in the mechanism of latex biosynthesis or polyisoprene chain elongation to act on the yield or molecular weight of latex, or a gene that is involved in the biosynthesis of a protein, sugar (e.g. inositol, quebrachitol), or tocotrienol (a vitamin E compound that is also effective as a natural antioxidant) in latex to affect the yield thereof, or a gene that can produce a mutant of the protein, sugar, or tocotrienol. Moreover, by incorporating a regulatory region (e.g. a promoter) that functions in a tissue-specific manner into such a gene, it is possible to express the protein encoded by the target gene in a specific tissue of the plant.

The target gene and the like include a target gene or a fragment thereof as well as a hygromycin-resistance gene as a marker gene. The target gene or fragment thereof may be incorporated into a vector along with the hygromycin-resistance gene and optionally a reporter gene.

The hygromycin-resistance gene serving as a marker gene refers to a gene encoding a selective marker that provides resistance to hygromycin present in a selective culture medium, which will be described later. This gene permits the transformed tissue fragment to grow even in a selective culture medium containing hygromycin, and thus to be selectively grown.

The reporter gene refers to a gene that can be incorporated to determine the expression site in the transgenic plant. Examples include luciferase gene, β-glucuronidase (GUS) gene, green fluorescent protein (GFP) gene, and red fluorescent protein (RFP) gene.

In the *Agrobacterium tumefaciens* preparation step, the *Agrobacterium tumefaciens* containing a plasmid containing a target gene and the like prepared as described above may be conventionally cultured (e.g., shake-cultured for 10 to 30 hours in YEB medium or LB medium at a culture temperature of 20 to 35° C.) and propagated to prepare an amount required to infect the tissue fragment.

Next, the tissue fragment from a *Taraxacum* plant to be infected with the *Agrobacterium tumefaciens* containing a plasmid containing a target gene and the like will be described. Any tissue fragment may be used, and examples include leaves, petioles, laminas, stems, nodes, roots, buds, axillary buds, apical buds, petals, cotyledons, hypocotyls, anthers, and seeds. Such a tissue fragment may be used as it is or may optionally be cultured to prepare a cultured tissue fragment before use. Further, the cultured tissue fragment may be mass propagated to increase the number before use. Moreover, the cultured tissue fragment may be further elongated before use.

<Infection Step>

The infection step includes infecting a tissue fragment from a *Taraxacum* plant with an *Agrobacterium tumefaciens* containing a plasmid containing a target gene or a fragment thereof and a hygromycin-resistance gene (the *Agrobacterium tumefaciens* obtained in the *Agrobacterium tumefaciens* preparation step).

The infection step can be carried out by procedures commonly used in *Agrobacterium* techniques. For example, infection may be accomplished by suspending the *Agrobacterium tumefaciens* in a liquid infection medium and immersing the tissue fragment in the suspension. After the immersion, the tissue fragment may be separated from the suspension using, for example, filter paper. The tissue fragment may be immersed under static or shaking conditions, but it is preferably immersed with shaking because this facilitates infection of the tissue fragment by the *Agrobacterium tumefaciens*.

The bacterial concentration in the *Agrobacterium tumefaciens* suspension used for infection may be selected as appropriate in view of the growth activity of the *Agrobacterium tumefaciens*, immersion time, and other factors. For example, an *Agrobacterium tumefaciens* population corresponding to 10 to 50 mL, preferably 20 to 40 mL, more preferably 25 to 35 mL, of an *Agrobacterium tumefaciens* suspension having an absorbance measured at 600 nm (OD600) of 0.01 to 1.0, preferably 0.05 to 0.8, more preferably 0.08 to 0.6, is preferably brought into contact with 100 tissue fragments. This can optimize the number of *Agrobacterium* cells that infect the tissue fragment to efficiently produce the transformant.

The *Agrobacterium tumefaciens*/tissue fragment coexistence time in the infection step, i.e., the time during which the tissue fragment is in contact with the *Agrobacterium tumefaciens*, is preferably 0.5 to 60 minutes, more preferably 1 to 40 minutes, still more preferably 5 to 35 minutes. This can optimize the number of *Agrobacterium* cells that infect the tissue fragment to efficiently produce the transformant. The coexistence time refers to, for example, the immersion time when the tissue fragment is immersed in the *Agrobacterium tumefaciens* suspension.

The infection medium in which the *Agrobacterium tumefaciens* is to be suspended may be prepared by adding a plant growth hormone and/or a carbon source, if necessary, to any of the following base media: basal media such as White's medium (disclosed on pp. 20-36 of Shokubutsu Saibo Kogaku Nyumon (Introduction to Plant Cell Engineering), Japan Scientific Societies Press), Heller's medium (Heller R, Bot. Biol. Veg. Paris 14, 1-223 (1953)), SH medium (Schenk and Hildebrandt medium), MS medium (Murashige and Skoog medium) (disclosed on pp. 20-36 of Shokubutsu Saibo Kogaku Nyumon (Introduction to Plant Cell Engineering), Japan Scientific Societies Press), LS medium (Linsmaier and Skoog medium) (disclosed on pp. 20-36 of Shokubutsu Saibo Kogaku Nyumon (Introduction to Plant Cell Engineering), Japan Scientific Societies Press), Gamborg medium, B5 medium (disclosed on pp. 20-36 of Shokubutsu Saibo Kogaku Nyumon (Introduction to Plant Cell Engineering), Japan Scientific Societies Press), MB medium, and WP medium (Woody Plant: for woody plants) (the disclosures of the foregoing documents are incorporated by reference herein), and modified basal media obtained by altering the composition of the basal media. Among these, MS medium, LS medium, B5 medium, and WP medium are preferred, with MS medium being more preferred. Examples of the plant growth hormone include auxin plant hormones and/or cytokinin plant hormones. The auxin plant hormones may be exemplified by 2,4-dichlorophenoxyacetic acid, 1-naphthaleneacetic acid, indole-3-butyric acid, indole-3-acetic acid, indolepropionic acid, chlorophenoxyacetic acid, naphthoxyacetic acid, phenylacetic acid, 2,4,5-trichlorophenoxyacetic acid, para-chlorophenoxyacetic acid, 2-methyl-4-chlorophenoxyacetic acid, 4-fluorophenoxyacetic acid, 2-methoxy-3,6-dichlorobenzoic acid, 2-phenyl acid, picloram, and picolinic acid. The cytokinin plant hormones may be exemplified by benzyladenine, kinetin, zeatin, benzylaminopurine, isopentenyl aminopurine, thidiazuron, isopentenyladenine, zeatin riboside, and dihydrozeatin. Any carbon source may be used, including sugars such as sucrose, glucose, trehalose, fructose, lactose, galactose, xylose, allose, talose, gulose, altrose, mannose, idose, arabinose, apiose, and maltose.

The suitable composition of the infection medium varies depending on the type of plant, but the composition, especially for *Taraxacum kok-saghyz*, is usually as follows.

The carbon source concentration in the infection medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 4 mass %. As used herein, the carbon source concentration means the sugar concentration.

Preferably, substantially no auxin or cytokinin plant hormone is added to the infection medium. In particular, the auxin and cytokinin plant hormone concentrations in the infection medium are each preferably not more than 1.0 mg/L, more preferably not more than 0.1 mg/L, still more preferably not more than 0.05 mg/L, particularly preferably not more than 0.01 mg/L.

In another preferred embodiment, the infection medium further contains acetosyringone (i.e., acetosyringone-containing medium) to facilitate infection of the tissue fragment by the *Agrobacterium tumefaciens*. When acetosyringone is added to the infection medium, the acetosyringone concentration in the infection medium is preferably 1 to 500 µM, more preferably 10 to 400 µM, still more preferably 50 to 250 µM.

The pH of the infection medium is not particularly critical, but is preferably 4.0 to 10.0, more preferably 5.0 to 6.0. The infection temperature (the temperature of the infection medium) is preferably 0 to 40° C., more preferably 20 to 36° C., still more preferably 22 to 30° C., most preferably 22 to 26° C. The infection step may be carried out in the dark or in the light. As used herein, the dark means that the illuminance is 0 to 0.1 lx, while the light means that the illuminance is more than 0.1 lx.

Among the conditions indicated above, it is particularly preferred that the infection medium contains substantially no plant growth hormone and has a pH of 5.0 to 6.0, and the culture temperature is 22 to 30° C.

As described above, in the infection step, the tissue fragment can be infected with the *Agrobacterium tumefaciens* obtained in the *Agrobacterium tumefaciens* preparation step, for example, by suspending the *Agrobacterium tumefaciens* in a liquid infection medium and immersing the tissue fragment in the suspension. After the immersion, the tissue fragment may preferably be separated from the suspension using, for example, filter paper, and then subjected to a subsequent co-culture step.

<Co-Culture Step>

An exemplary co-culture step includes culturing the tissue fragment obtained in the infection step (the tissue fragment infected with the *Agrobacterium tumefaciens*) in a co-culture medium. This allows the gene fragment containing the target gene and the like which has been introduced into the tissue fragment by infection to be incorporated into the genes of the plant cells to produce a more stable transformant.

The co-culture medium may be a liquid or a solid, but solid culture is preferred because a stable transformant can be produced by plating on the medium. When the co-culture medium is a liquid medium, static culture or shake culture may be performed. When the co-culture medium is prepared as a solid medium, the medium may be converted to a solid using a solidifying agent. Non-limiting examples of the solidifying agent include agar, gellan gum (e.g. Gelrite), agarose, gelatin, and silica gel.

The co-culture medium may be prepared by adding a plant growth hormone and/or a carbon source, if necessary, to a base medium (e.g., any of the listed basal media and modified basal media obtained by altering the composition of the basal media). MS medium, LS medium, B5 medium, and WP medium, among others, are preferred. More preferred are MS medium and modified MS media obtained by altering the composition of MS medium. Suitable plant growth hormones and carbon sources are those listed for the infection medium.

The suitable composition of the co-culture medium varies depending on the type of plant, but the composition, especially for *Taraxacum kok-saghyz*, is usually as follows.

The carbon source concentration in the co-culture medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 4 mass %.

When an auxin plant hormone is added to the co-culture medium, the auxin plant hormone concentration in the co-culture medium is preferably at least 0.01 mg/L, more preferably at least 0.05 mg/L, still more preferably at least 0.1 mg/L. The auxin plant hormone concentration is preferably not more than 5.0 mg/L, more preferably not more than 1.0 mg/L.

When a cytokinin plant hormone is added to the co-culture medium, the cytokinin plant hormone concentration in the co-culture medium is preferably at least 0.01 mg/L, more preferably at least 0.1 mg/L, still more preferably at least 0.5 mg/L, particularly preferably at least 0.8 mg/L. The cytokinin plant hormone concentration is preferably not more than 7.0 mg/L, more preferably not more than 6.0 mg/L.

The co-culture medium may further contain acetosyringone (i.e., acetosyringone-containing medium) to further facilitate production of a stable transformant. The acetosyringone concentration in the co-culture medium is preferably 1 to 500 µM, more preferably 10 to 400 µM, still more preferably 50 to 250 µM.

When the co-culture medium is a solid medium, the solidifying agent concentration in the co-culture medium is preferably at least 0.1 mass %, more preferably at least 0.2 mass %, still more preferably at least 0.5 mass %. The solidifying agent concentration is preferably not more than 2 mass %, more preferably not more than 1.1 mass %, still more preferably not more than 0.8 mass %.

The pH of the co-culture medium is not particularly critical, but is preferably 4.0 to 10.0, more preferably 5.0 to 6.0. As used herein, the pH of the solid medium means the pH of the medium that incorporates all the components except the solidifying agent.

The culture temperature is preferably 0 to 40° C., more preferably 10 to 36° C., still more preferably 20 to 28° C., most preferably 22 to 25° C. Culture may be carried out in the dark or in the light, and preferably in the dark where the illuminance is preferably 0 to 0.1 lx. The culture time is not particularly critical, but is preferably 2 to 4 days.

Among the conditions indicated above, it is particularly preferred that the plant growth hormone includes an auxin plant hormone (particularly 1-naphthaleneacetic acid) and a cytokinin plant hormone (particularly benzyladenine) at concentrations of 0.1 to 1.0 mg/L and 0.8 to 6.0 mg/L, respectively, and the culture temperature is 20 to 28° C.

As described above, in the co-culture step, a more stable transformant can be produced by culturing the tissue fragment obtained in the infection step (the tissue fragment infected with the *Agrobacterium tumefaciens*) in the co-culture medium so that the gene fragment containing the target gene and the like which has been introduced into the tissue fragment by infection can be incorporated into the genes of the plant cells. The tissue fragment obtained in the co-culture step (a mixture of the transformed and untransformed tissue fragments) is preferably subjected to the subsequent selective culture step.

<Selective Culture Step>

The selective culture step includes selecting the tissue fragment that has acquired the target gene from the tissue fragment obtained in the infection step (or the tissue fragment obtained in the co-culture step, if performed after the infection step) by using hygromycin. Thus, it includes culturing the tissue fragment obtained in the infection step in a selective culture medium containing hygromycin to select the tissue fragment that has acquired the target gene.

The selective culture step can be carried out by procedures commonly used in *Agrobacterium* techniques. This step allows the transformed tissue fragment to be screened from the untransformed tissue fragment.

The selective culture step preferably includes culturing the tissue fragment obtained in the infection step in a selective culture medium containing 0.1 to 2 mg/L of hygromycin to select the tissue fragment that has acquired the target gene. When the hygromycin concentration in the selective culture medium falls within the above range, the transformant can be more efficiently screened.

In the selective culture step, it is preferred to first wash the tissue fragment obtained in the infection step (or the tissue fragment obtained in the co-culture step, if performed after the infection step) (a mixture of the transformed and untransformed tissue fragments) with a base medium (e.g., any of the listed basal media and modified basal media obtained by altering the composition of the basal media) supplemented with an antibiotic (disinfectant) such as carbenicillin or Augmentin in order to sterilize the *Agrobacterium tumefaciens*. Before the sterilization, the tissue fragment obtained in the infection step (or the tissue fragment obtained in the co-culture step, if performed after the infection step) (a mixture of the transformed and untransformed tissue fragments) may be washed beforehand with a base medium (e.g., any of the listed basal media and modified basal media obtained by altering the composition of the basal media).

Next, the tissue fragment sterilized with the antibiotic is cultured in the selective culture medium. The culture conditions in the selective culture step are not particularly critical as long as they allow the transformed tissue fragment (the tissue fragment that has acquired the target gene) to be selectively grown.

The selective culture medium may be a liquid or a solid. When the selective culture medium is a liquid medium, static culture or shake culture may be performed.

The selective culture medium may be prepared by adding hygromycin to a base medium (e.g., any of the listed basal media and modified basal media obtained by altering the composition of the basal media). It is preferred to add hygromycin to MS medium, LS medium, B5 medium, or WP medium, more preferably MS medium, among others. The medium may be supplemented with an antibiotic such as Augmentin, if necessary. Moreover, a plant growth hormone and/or a carbon source may also be added, if necessary. Suitable plant growth hormones and carbon sources are those listed for the infection medium.

As described above, the tissue fragment (sterilized with the antibiotic) (a mixture of the transformed and untransformed tissue fragments) is cultured in a selective culture medium supplemented with hygromycin, where the transformed tissue fragment into which a target gene and a gene resistant to hygromycin (hygromycin-resistance gene) have been introduced can then grow, while the untransformed tissue fragment will not grow. Thus, the transformed tissue fragment can be selectively grown by culturing a mixture of the transformed and untransformed tissue fragments in a medium supplemented with hygromycin.

The hygromycin concentration in the selective culture medium is preferably 0.1 to 2 mg/L. It is more preferably at least 0.3 mg/L, still more preferably at least 0.5 mg/L, but is more preferably not more than 5 mg/L, still more preferably not more than 1.0 mg/L.

The suitable composition of the selective culture medium varies depending on the type of plant, but the composition, especially for *Taraxacum kok-saghyz*, is usually as follows.

The carbon source concentration in the selective culture medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 5 mass %, further preferably not more than 4 mass %.

When an auxin plant hormone is added to the selective culture medium, the auxin plant hormone concentration in the selective culture medium is preferably at least 0.01 mg/L, more preferably at least 0.05 mg/L, still more preferably at least 0.1 mg/L. The auxin plant hormone concentration is preferably not more than 5.0 mg/L, more preferably not more than 1.0 mg/L.

When a cytokinin plant hormone is added to the selective culture medium, the cytokinin plant hormone concentration in the selective culture medium is preferably at least 0.01 mg/L, more preferably at least 0.1 mg/L, still more preferably at least 0.5 mg/L. The cytokinin plant hormone concentration is preferably not more than 7.0 mg/L, more preferably not more than 6.0 mg/L.

When the selective culture medium is prepared as a solid medium, the medium may be converted to a solid using a solidifying agent as described for the co-culture medium.

When the selective culture medium is a solid medium, the solidifying agent concentration in the selective culture medium is preferably at least 0.1 mass %, more preferably at least 0.2 mass %, still more preferably at least 0.5 mass %. The solidifying agent concentration is preferably not more than 2 mass %, more preferably not more than 1.1 mass %, still more preferably not more than 0.8 mass %.

The pH of the selective culture medium is not particularly critical, but is preferably 5.0 to 7.0, more preferably 5.6 to 6.5.

Culture in the selective culture medium is usually carried out in a controlled environment in which culture conditions such as temperature and photoperiod are managed. The culture conditions may be selected as appropriate, but for example the culture temperature is preferably 0 to 40° C., more preferably 20 to 40° C., still more preferably 25 to 35° C. Culture may be carried out in the dark or in the light, and suitable light conditions include, for example, a 10-16 h photoperiod at 1,000 to 50,000 lx. The culture time is not particularly critical as long as the effects are achieved, but culture is preferably carried out for 1 to 20 weeks, more preferably 2 to 18 weeks, still more preferably 4 to 15 weeks. Moreover, subculture is preferably performed at one to four-week intervals.

Among the conditions indicated above, it is particularly preferred that the plant growth hormone includes an auxin plant hormone (particularly 1-naphthaleneacetic acid) and a cytokinin plant hormone (particularly benzyladenine) at concentrations of 0.1 to 1.0 mg/L and 0.5 to 6.0 mg/L, respectively, the hygromycin concentration is 0.1 to 2 mg/L, and the culture temperature is 25 to 35° C.

As described above, in the selective culture step, the tissue fragment obtained in the infection step (or the tissue fragment obtained in the co-culture step, if performed after the infection step) (a mixture of the transformed and untransformed tissue fragments) may optionally be washed with an antibiotic to sterilize the *Agrobacterium tumefaciens*. Next, by culturing the tissue fragment in the selective culture medium, the transformed tissue fragment can be selectively grown and screened from the untransformed tissue fragment. The tissue fragment (transformed tissue fragment) screened in this selective culture step is subjected to the subsequent callus-inducing step.

<Callus-Inducing Step>

The callus-inducing step includes culturing the tissue fragment obtained in the selective culture step in a callus-inducing medium containing a cytokinin plant hormone, an auxin plant hormone, and a carbon source to form callus (or induce callus). The callus-inducing medium may be a liquid or a solid, but solid culture is preferred because callus formation is facilitated by plating on the medium. When the callus-inducing medium is a liquid medium, static culture or shake culture may be performed.

The callus-inducing medium may be prepared by adding a cytokinin plant hormone, an auxin plant hormone, and a carbon source to a base medium (e.g., any of the listed basal media and modified basal media obtained by altering the composition of the basal media). MS medium, LS medium, B5 medium, and WP medium, among others, are preferred. More preferred are MS medium and modified MS media obtained by altering the composition of MS medium. Suitable cytokinin plant hormones, auxin plant hormones, and carbon sources are those listed for the infection medium.

The callus-inducing medium may contain at least one selected from the group consisting of jasmonic acid and monoterpene compounds.

Examples of the monoterpene compounds include D-limonene, α-pinene, β-pinene, l-menthol, geraniol, carane, pinane, myrcene, ocimene, and cosmene. Among the foregoing, D-limonene or α-pinene is preferred.

The suitable composition of the callus-inducing medium varies depending on the type of plant, but the composition, especially for *Taraxacum kok-saghyz*, is usually as follows.

The carbon source concentration in the callus-inducing medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 5 mass %, further preferably not more than 4 mass %.

The auxin plant hormone concentration in the callus-inducing medium is preferably less than 1.2 mg/L, more preferably not more than 1.0 mg/L. The auxin plant hormone concentration is preferably at least 0.01 mg/L, more preferably at least 0.05 mg/L, still more preferably at least 0.1 mg/L.

The cytokinin plant hormone concentration in the callus-inducing medium is preferably at least 0.01 mg/L, more preferably at least 0.1 mg/L, still more preferably at least 0.5 mg/L. The cytokinin plant hormone concentration is preferably not more than 1.2 mg/L, more preferably not more than 1.0 mg/L.

When the callus-inducing medium is prepared as a solid medium, the medium may be converted to a solid using a solidifying agent as described for the co-culture medium.

When the callus-inducing medium is a solid medium, the solidifying agent concentration in the callus-inducing medium is preferably at least 0.1 mass %, more preferably at least 0.2 mass %, still more preferably at least 0.5 mass %. The solidifying agent concentration is preferably not more than 2 mass %, more preferably not more than 1.1 mass %, still more preferably not more than 0.8 mass %.

The pH of the callus-inducing medium is not particularly critical, but is preferably 4.0 to 10.0, more preferably 5.6 to 6.5.

The culture temperature is preferably 0 to 40° C., more preferably 20 to 26° C. Culture may be carried out in the dark or in the light, and suitable light conditions include, for example, a 10-16 h photoperiod at 1,000 to 50,000 lx. The culture time may be 1 to 7 weeks, preferably 1 to 6 weeks, more preferably 1 to 5 weeks.

Among the conditions indicated above, it is particularly preferred that the auxin plant hormone (particularly 1-naphthaleneacetic acid) concentration is less than 1.2 mg/L, the cytokinin plant hormone (particularly benzyladenine) concentration is 0.5 to 1.2 mg/L, and the culture temperature is 20 to 26° C.

As described above, callus induction can be accomplished by culturing the tissue fragment obtained in the selective culture step in the callus-inducing medium. The callus obtained in this callus-inducing step is subjected to the subsequent regeneration-inducing step, but in order to propagate a larger amount of plants, the induced callus may first be grown and then subjected to the regeneration-inducing step. The growth of the callus may be carried out by culturing the callus under conditions that allow the callus to grow. For example, the callus may be grown by culturing using the same medium composition and culture conditions as in the callus-inducing step.

<Regeneration-Inducing Step>

The regeneration-inducing step includes culturing the callus obtained in the callus-inducing step in a regeneration-inducing medium containing a plant growth hormone and a carbon source to form an adventitious embryo, an adventitious bud, and a shoot. Since it is possible to stably form a shoot via adventitious bud formation by inducing (forming) an adventitious embryo from the callus and culturing the adventitious embryo, the culture conditions in the regeneration-inducing step are not particularly critical as long as they can induce an adventitious embryo from the callus.

In the regeneration-inducing step, for example, the callus induced by the callus-inducing step may be cultured in a regeneration-inducing medium to induce an adventitious embryo. The regeneration-inducing medium may be a liquid or a solid, but solid culture is preferred because adventitious embryo induction is facilitated by plating on the medium. When the regeneration-inducing medium is a liquid medium, static culture or shake culture may be performed.

The regeneration-inducing medium may be prepared by adding a plant growth hormone and a carbon source to a base medium (e.g., any of the listed basal media and modified basal media obtained by altering the composition of the basal media). MS medium, LS medium, B5 medium, and WP medium, among others, are preferred. More preferred are MS medium and modified MS media obtained by altering the composition of MS medium. Suitable plant growth hormones and carbon sources are those listed for the infection medium. The plant growth hormone preferably includes an auxin plant hormone and a cytokinin plant hormone, more preferably 1-naphthaleneacetic acid and benzyladenine, because they are suitable for inducing an adventitious embryo.

The suitable composition of the regeneration-inducing medium varies depending on the type of plant, but the composition, especially for *Taraxacum kok-saghyz*, is usually as follows.

The carbon source concentration in the regeneration-inducing medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 5 mass %, further preferably not more than 4 mass %.

The auxin plant hormone concentration in the regeneration-inducing medium is preferably less than 0.2 mg/L, more preferably not more than 0.1 mg/L. The auxin plant hormone concentration is preferably at least 0.01 mg/L, more preferably at least 0.05 mg/L, still more preferably at least 0.07 mg/L.

The cytokinin plant hormone concentration in the regeneration-inducing medium is preferably at least 0.1 mg/L, more preferably at least 0.4 mg/L, still more preferably at least 0.5 mg/L. The cytokinin plant hormone concentration is preferably not more than 1.2 mg/L, more preferably not more than 1.1 mg/L, still more preferably not more than 1.0 mg/L.

When the regeneration-inducing medium is prepared as a solid medium, the medium may be converted to a solid using a solidifying agent as described for the co-culture medium.

When the regeneration-inducing medium is a solid medium, the solidifying agent concentration in the regeneration-inducing medium is preferably at least 0.1 mass %, more preferably at least 0.2 mass %, still more preferably at least 0.5 mass %. The solidifying agent concentration is preferably not more than 2 mass %, more preferably not more than 1.1 mass %, still more preferably not more than 0.8 mass %.

FeNaEDTA may be added to the regeneration-inducing medium to prevent accumulation of growth inhibitors in the tissue. Moreover, gibberellin may be added to promote adventitious embryo formation. In addition, an antibiotic (disinfectant) such as carbenicillin or Augmentin, or hygromycin may be added.

The pH of the regeneration-inducing medium is not particularly critical, but is preferably 4.0 to 10.0, more preferably 5.6 to 6.5.

The culture temperature is preferably 0 to 40° C., more preferably 20 to 36° C., still more preferably 23 to 32° C. Culture may be carried out in the dark or in the light, and suitable light conditions include, for example, a 10-16 h photoperiod at 1,000 to 50,000 lx. The culture time is not particularly critical, but is preferably 1 to 10 weeks, more preferably 4 to 10 weeks.

Among the conditions indicated above, it is particularly preferred that the auxin plant hormone (particularly 1-naphthaleneacetic acid) concentration is less than 0.2 mg/L, the cytokinin plant hormone (particularly benzyladenine) concentration is 0.4 to 1.1 mg/L, and the culture temperature is 23 to 32° C.

As described above, in the regeneration-inducing step, an adventitious embryo, an adventitious bud, and a shoot can be formed by culturing the callus obtained in the callus-inducing step in the regeneration-inducing medium. The shoot formed in this regeneration-inducing step is subjected to the subsequent rooting step, but before the rooting step the formed shoot may be further elongated. The elongation of the shoot may be carried out by culturing the shoot under conditions that allow the shoot to elongate. For example, the shoot may be elongated by culturing using the same medium composition and culture conditions as in the regeneration-inducing step.

<Rooting Step>

The rooting step includes culturing the shoot obtained in the regeneration-inducing step in a rooting medium to root the shoot.

In the rooting step, for example, the shoot formed by the regeneration-inducing step may be cultured in a rooting medium to root the shoot. The rooting medium may be a liquid or a solid, but solid culture is preferred because rooting is facilitated by plating on the medium. When the rooting medium is a liquid medium, static culture or shake culture may be performed.

The rooting medium may be prepared by adding a carbon source and optionally a plant growth hormone to a base medium (e.g., any of the listed basal media and modified basal media obtained by altering the composition of the basal media). MS medium, LS medium, B5 medium, and WP medium, among others, are preferred. More preferred are MS medium and modified MS media obtained by altering the composition of MS medium. Suitable plant growth hormones and carbon sources are those listed for the infection medium. However, the rooting medium is preferably free from any plant growth hormone to suitably root the shoot.

The suitable composition of the rooting medium varies depending on the type of plant, but the composition, especially for *Taraxacum kok-saghyz*, is usually as follows.

The carbon source concentration in the rooting medium is preferably at least 0.1 mass %, more preferably at least 1 mass %, still more preferably at least 2 mass %, particularly preferably at least 3 mass %. The carbon source concentration is preferably not more than 10 mass %, more preferably not more than 6 mass %, still more preferably not more than 5 mass %, further preferably not more than 4 mass %.

Preferably, substantially no auxin or cytokinin plant hormone is added to the rooting medium. In particular, the auxin and cytokinin plant hormone concentrations in the rooting medium are each preferably not more than 1.0 mg/L, more preferably not more than 0.1 mg/L, still more preferably not more than 0.05 mg/L, particularly preferably not more than 0.01 mg/L.

When the rooting medium is prepared as a solid medium, the medium may be converted to a solid using a solidifying agent as described for the co-culture medium.

When the rooting medium is a solid medium, the solidifying agent concentration in the rooting medium is preferably at least 0.1 mass %, more preferably at least 0.2 mass %, still more preferably at least 0.5 mass %. The solidifying agent concentration is preferably not more than 2 mass %, more preferably not more than 1.1 mass %, still more preferably not more than 0.8 mass %.

An antibiotic (disinfectant) such as carbenicillin or Augmentin may be added to the rooting medium to suitably root the shoot.

The pH of the rooting medium is not particularly critical, but is preferably 4.0 to 10.0, more preferably 5.6 to 6.5.

The culture temperature is preferably 0 to 40° C., more preferably 10 to 36° C., still more preferably 20 to 30° C. Culture may be carried out in the dark or in the light, and suitable light conditions include, for example, a 10-16 h photoperiod at 1,000 to 50,000 lx. The culture time is not particularly critical, but is preferably 1 to 10 weeks, more preferably 2 to 8 weeks.

Among the conditions indicated above, it is particularly preferred that that the rooting medium contains substantially no plant growth hormone, and the culture temperature is 20 to 30° C.

As described above, in the rooting step, the shoot obtained in the regeneration-inducing step can be rooted by culturing in the rooting medium. Thus, the rooted shoot (plantlet) can be obtained. The plantlet may be transplanted directly to soil, but is preferably acclimatized, e.g., transferred to an artificial soil such as vermiculite, before the transplantation to soil.

As described, the production method of the present invention includes an infection step of infecting a tissue fragment from a *Taraxacum* plant with an *Agrobacterium tumefaciens* containing a plasmid containing a target gene or a fragment thereof and a hygromycin-resistance gene; a selective culture step of selecting the tissue fragment that has acquired the target gene from the tissue fragment obtained in the infection step by using hygromycin; a callus-inducing step of culturing the tissue fragment obtained in the selective culture step in a callus-inducing medium containing a cytokinin plant hormone, an auxin plant hormone, and a carbon source to form callus; a regeneration-inducing step of culturing the callus obtained in the callus-inducing step in a regeneration-inducing medium containing a plant growth hormone and a carbon source to form an adventitious embryo, an adventitious bud, and a shoot; and a rooting step of culturing the shoot obtained in the regeneration-inducing step in a rooting medium to root the shoot. Thus, it is possible to efficiently produce a transgenic *Taraxacum* plant in a short period of time.

Whether the thus regenerated (produced) transgenic plant has actually been transformed can be determined by conventional methods, such as by performing DNA extraction from the plant followed by PCR analysis of whether the target gene and the like have been introduced, or by further incorporating a reporter gene, e.g. GUS gene or GFP gene, into the vector followed by GUS or GFP observation.

EXAMPLES

The present invention is specifically described with reference to examples, but the present invention is not limited only to these.

The chemicals used in the examples are listed below.

Gelrite: Wako Pure Chemical Industries, Ltd.

Acetosyringone: Tokyo Chemical Industry Co., Ltd.

NAA: 1-naphthaleneacetic acid

BA: benzyladenine

Hygromycin: Wako Pure Chemical Industries, Ltd.

Augmentin: GlaxoSmithKline

Example 1

[Seeding/Dormancy-Breaking/Rooting/Cultivation]

Two or three pieces of filter paper were stacked and placed on a dish and moistened with deionized water. Seeds of *Taraxacum kok-saghyz* (available from United States Department of Agriculture, Animal and Plant Health Inspection Service, Plant Protection and Quarantine) were placed at intervals of 1.5 cm or more from each other on the filter paper. The dish was covered with a lid and sealed with a parafilm. The dish was placed in a refrigerator (4° C.) for 3 days to break dormancy. After the dormancy-breaking treatment, the seeds were plated on a germination medium and placed in an incubator at 16 to 22° C. The germination medium was prepared by adding 20 g/L of sucrose to MS medium (disclosed on pp. 20-36 of Shokubutsu Saibo Kogaku Nyumon (Introduction to Plant Cell Engineering), Japan Scientific Societies Press) and adjusting the pH of the medium to 5.8, followed by addition of 3 g/L of Gelrite, sterilization in an autoclave (at 121° C. for 20 minutes), and then cooling in a clean bench.

[*Agrobacterium tumefaciens* Preparation Step]

A plasmid into which a target gene had been inserted along with a hygromycin-resistance gene was introduced into *Agrobacterium tumefaciens* (EHA105) by electroporation. The *Agrobacterium tumefaciens* was shake-cultured overnight in liquid LB medium at a culture temperature of 28° C. Culture was continued until the absorbance measured at 600 nm (OD600) reached about 1.0. The bacteria were then collected by centrifugal separation, followed by adjustment to OD600=0.1 to 0.2 using a suspending solution (infection medium; liquid MS medium supplemented with 0.1 mmol/L of acetosyringone, 0.01 mmol/L of mercaptoethanol, and 30 g/L of sucrose and adjusted to pH 5.8). The absorbance was measured by Nano Drop 2000c available from Thermo Scientific.

[Infection Step, Co-Culture Step]

The cotyledons cultivated for one month after germination of the plant were cut to a width of 5 mm (100 pieces) and left at 25° C. for 5 to 10 minutes in 40 mL of the infection medium in which the *Agrobacterium tumefaciens* was suspended (infection step). Then, the excess of the *Agrobacterium tumefaciens* suspension adhered to the cotyledon pieces was removed, and the cotyledon pieces were plated on a co-culture medium with their adaxial surfaces facing downwards, and then co-cultured for 2 days in the dark (at an illuminance of less than 0.1 lx) at a culture temperature of 25° C. (co-culture step).

The co-culture medium was prepared by adding benzyladenine (BA), 1-naphthaleneacetic acid (NAA), and sucrose at 1.0 mg/L, 0.1 mg/L, and 30 g/L, respectively, to MS medium and adjusting the pH of the medium to 5.8, followed by addition of 3 g/L of Gelrite, sterilization in an autoclave (at 121° C. for 20 minutes), and then cooling in a clean bench.

[Selective Culture Step]

The co-cultured cotyledon pieces were collected, transplanted in the hygromycin-containing selective culture medium indicated in Table 1, and cultured for 4 weeks with a 16 h/24 h photoperiod (2,000 lx) at a culture temperature of 25° C. Medium exchange was performed every other week.

The selective culture medium was prepared by adding benzyladenine (BA), 1-naphthaleneacetic acid (NAA), Augmentin, hygromycin, and sucrose at the respective concentrations indicated in Table 1 to MS medium and adjusting the pH of the medium to 5.8, followed by addition of 3 g/L of Gelrite, sterilization in an autoclave (at 121° C. for 20 minutes), and then cooling in a clean bench.

[Callus-Inducing Step]

The cotyledon pieces screened in the selective culture step were transplanted in a callus-inducing medium and cultured for one week with a 16 h/24 h photoperiod (2,000 lx) at a culture temperature of 25° C. As a result of the culturing, it was observed that callus was induced from some cotyledon pieces.

The callus-inducing medium was prepared by adding benzyladenine (BA), 1-naphthaleneacetic acid (NAA), and sucrose at 0.5 mg/L, 0.1 mg/L, and 30 g/L, respectively, to MS medium and adjusting the pH of the medium to 5.8, followed by addition of 3 g/L of Gelrite, sterilization in an autoclave (at 121° C. for 20 minutes), and then cooling in a clean bench.

[Regeneration-Inducing Step]

The callus produced from the cotyledon pieces in the callus-inducing step was transplanted in a regeneration-inducing medium and cultured for 4 weeks with a 16 h/24 h photoperiod (2,000 lx) at a culture temperature of 25° C. Medium exchange was performed every two weeks. As a result of the culturing, it was observed that an adventitious embryo and then a shoot (adventitious bud) were formed from some pieces of callus.

The regeneration-inducing medium was prepared by adding benzyladenine (BA), 1-naphthaleneacetic acid (NAA), Augmentin, hygromycin, and sucrose at 0.5 mg/L, 0.1 mg/L, 375 mg/L, 0.5 mg/L, and 30 g/L, respectively, to MS medium and adjusting the pH of the medium to 5.8, followed by addition of 3 g/L of Gelrite, sterilization in an autoclave (at 121° C. for 20 minutes), and then cooling in a clean bench.

[Rooting Step]

Figure 1B:
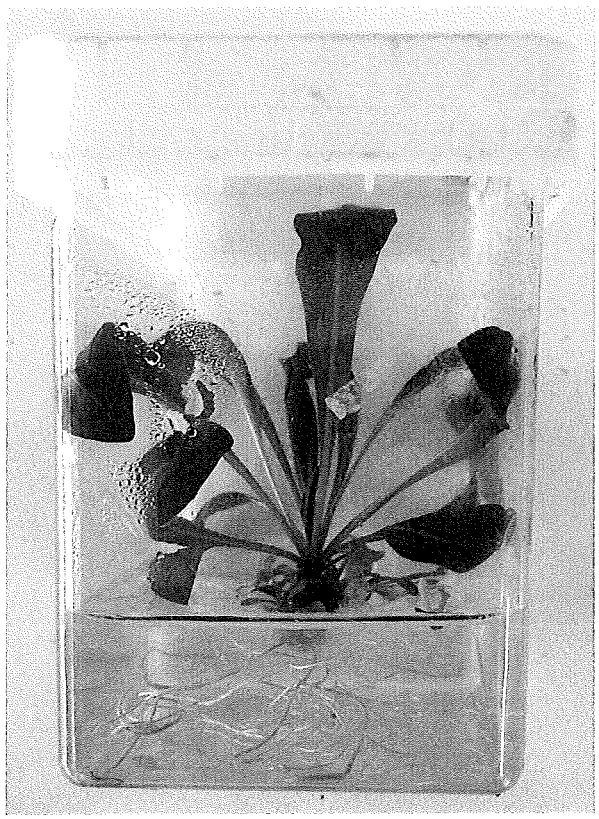

The shoot (adventitious bud) of about 1 to 2 cm in length produced from the callus in the regeneration-inducing step was cut out of the callus, transplanted in a rooting medium, and cultured for 3 weeks with a 16 h/24 h photoperiod (2,000 lx) at a culture temperature of 25° C. As a result of the culturing, it was observed that some shoots were rooted to produce regenerated plants. FIGS. 1A and 1B are photographs showing the appearance of the regenerated plants.

The rooting medium was prepared by adding Augmentin and sucrose at 375 mg/L and 30 g/L, respectively, to MS medium and adjusting the pH of the medium to 5.8, followed by addition of 3 g/L of Gelrite, sterilization in an autoclave (at 121° C. for 20 minutes), and then cooling in a clean bench.

TABLE 1

|  |  | Example 1 |
|---|---|---|
| Selective culture medium | MS medium | MS medium |
|  | Benzyladenine (BA)[mg/L] | 0.5 |
|  | 1-Naphthaleneacetic acid (NAA)[mg/L] | 0.1 |
|  | Augmentin [mg/L] | 375 |
|  | Hygromycin [mg/L] | 0.5 |
|  | Sucrose [g/L] | 30 |
|  | Gelrite [g/L] | 3 |
|  | Number (count) of regenerants | 25 |

[Confirmation of Gene Introduction in Regenerant]

Whether the gene had been introduced in the regenerants was confirmed as follows. DNA was extracted by the CTAB method from a part of the leaves of the regenerated plants having been rooted in Example 1, and a PCR reaction was performed using the extracted DNA as a template and the hygromycin-resistance gene-specific primers listed below. The PCR reaction was initiated at 94° C. for 3 min, followed by 35 cycles of 94° C. for 30 sec, 55° C. for 30 sec, and 72° C. for 1 min, followed by a final step at 72° C. for 10 min. Then, a part of the solution after the PCR reaction was subjected to agarose gel electrophoresis to confirm the gene introduction.

```
Primer 1 (Hyg-F):
                                   (SEQ ID NO: 1)
5'-GCTGATCCCCATGTGTATCACTGGC-3'

Primer 2 (Hyg-R):
                                   (SEQ ID NO: 2)
5'-CTATTCCTTTGCCCTCGGACGAGTGC-3'
```

Figure 2:
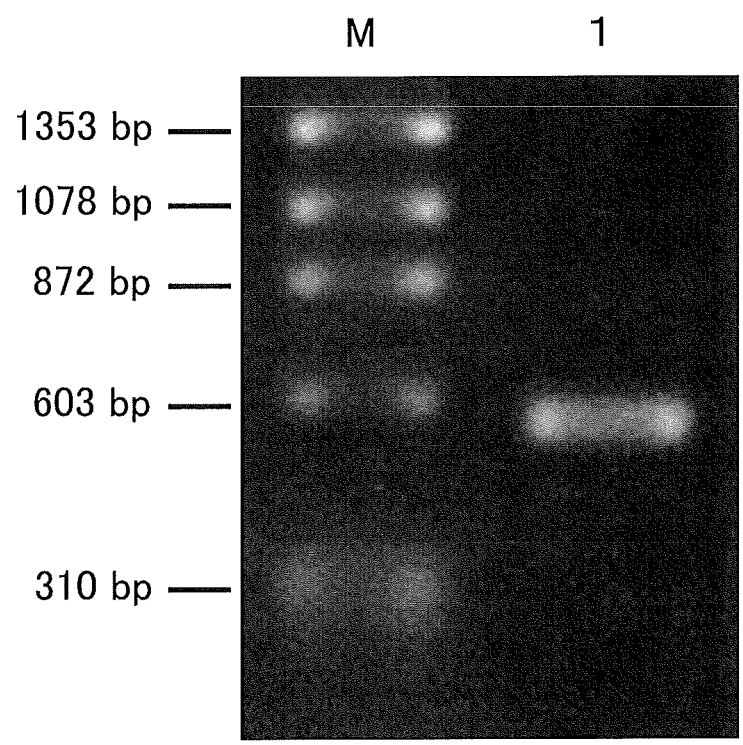
FIG. 2 is a photograph representing the agarose gel electrophoresis results of Example 1.

FIG. 2 is a photograph representing the agarose gel electrophoresis results of Example 1. FIG. 2 confirmed that the hygromycin-resistance gene had been inserted in the regenerated plant having been rooted in Example 1. The results demonstrated that the regenerated plant having been rooted in Example 1 was a transgenic plant.

Reference Examples 11 to 16, Comparative Reference Example 17

[Seeding/Ddormancy-Breaking/Rooting/Cultivation]

Two or three pieces of filter paper were stacked and placed on a dish and moistened with deionized water. Seeds of *Taraxacum kok-saghyz* (available from United States Department of Agriculture, Animal and Plant Health Inspection Service, Plant Protection and Quarantine) were placed at intervals of 1.5 cm or more from each other on the filter paper. The dish was covered with a lid and sealed with a parafilm. The dish was placed in a refrigerator (4° C.) for 3 days to break dormancy. After the dormancy-breaking treatment, the seeds were plated on a germination medium and placed in an incubator at 16 to 22° C. The germination medium was prepared by adding 20 g/L of sucrose to MS medium and adjusting the pH of the medium to 5.8, followed by addition of 3 g/L of Gelrite, sterilization in an autoclave (at 121° C. for 20 minutes), and then cooling in a clean bench.

[Callus-Inducing Step]

The cotyledons cultivated for one month after germination of the plant were cut to a width of 5 mm, and the cotyledon pieces were plated on a callus-inducing medium with their adaxial surfaces facing downwards, and then cultured for 4 weeks with a 16 h/24 h photoperiod (2,000 lx) at a culture temperature of 25° C. The medium was replaced with fresh one every two weeks.

The callus-inducing medium was prepared by adding benzyladenine (BA), 1-naphthaleneacetic acid (NAA), and sucrose at the respective concentrations indicated in Table 2 to MS medium and adjusting the pH of the medium to 5.8, followed by addition of 3 g/L of Gelrite, sterilization in an autoclave (at 121° C. for 20 minutes), and then cooling in a clean bench.

[Induction Success Rate]

In Reference Examples (Ref. Ex.) 11 to 16 and Comparative Reference Example (Comp. Ref. Ex.) 17, the number of cotyledon pieces from which callus had been induced was counted to determine induction success rate. Table 2 shows the results.

Induction success rate (%)=[Number (count) of cotyledon pieces that succeeded in callus induction]/[Number (count) of tested cotyledon pieces]×100 medium and adjusting the pH of the medium to 5.8, followed by addition of 3 g/L of Gelrite, sterilization in an autoclave (at 121° C. for 20 minutes), and then cooling in a clean bench.

[Callus-Inducing Step]

The cotyledons cultivated for one month after germination of the plant were cut to a width of 5 mm, and the cotyledon pieces were plated on a callus-inducing medium with their adaxial surfaces facing downwards, and then cultured for 4 weeks with a 16 h/24 h photoperiod (2,000 lx) at a culture temperature of 25° C. The medium was replaced with fresh one every two weeks.

The callus-inducing medium was prepared by adding benzyladenine (BA), 1-naphthaleneacetic acid (NAA), and sucrose at 0.5 mg/L, 0.1 mg/L, and 20 g/L, respectively, to MS medium and adjusting the pH of the medium to 5.8, followed by addition of 3 g/L of Gelrite, sterilization in an autoclave (at 121° C. for 20 minutes), and then cooling in a clean bench.

[Regeneration-Inducing Step]

The callus produced from the cotyledon pieces in the callus-inducing step was transplanted in a regeneration-inducing medium and cultured for 4 weeks with a 16 h/24 h photoperiod (2,000 lx) at a culture temperature of 25° C. The medium was replaced with fresh one every two weeks.

TABLE 2

|  |  | Ref. Ex. 11 | Ref. Ex. 12 | Ref. Ex. 13 | Ref. Ex. 14 | Ref. Ex. 15 | Ref. Ex. 16 | Comp. Ref. Ex. 17 |
|---|---|---|---|---|---|---|---|---|
| Callus-inducing medium | MS medium | MS medium | MS medium | MS medium | MS medium | MS medium | MS medium | MS medium |
|  | Benzyladenine (BA)[mg/L] | 0.5 | 0.5 | 0.5 | 1.0 | 1.0 | 1.0 | 0 |
|  | 1-Naphthaleneacetic acid (NAA)[mg/L] | 0.1 | 0.5 | 1.0 | 0.1 | 0.5 | 1.0 | 0 |
|  | Sucrose [g/L] | 20 | 20 | 20 | 20 | 20 | 20 | 20 |
|  | Gelrite [g/L] | 3 | 3 | 3 | 3 | 3 | 3 | 3 |
| Number (count) of tested cotyledon pieces |  | 26 | 24 | 23 | 25 | 25 | 25 | 26 |
| Number (count) of cotyledon pieces that succeeded in callus induction |  | 26 | 24 | 23 | 25 | 25 | 25 | 2 |
| Induction success rate (%) |  | 100 | 100 | 100 | 100 | 100 | 100 | 7.7 |

Reference Examples 21 and 22, Comparative Reference Example 23

[Seeding/Dormancy-Breaking/Rooting/Cultivation]

Two or three pieces of filter paper were stacked and placed on a dish and moistened with deionized water. Seeds of *Taraxacum kok-saghyz* (available from United States Department of Agriculture, Animal and Plant Health Inspection Service, Plant Protection and Quarantine) were placed at intervals of 1.5 cm or more from each other on the filter paper. The dish was covered with a lid and sealed with a parafilm. The dish was placed in a refrigerator (4° C.) for 3 days to break dormancy. After the dormancy-breaking treatment, the seeds were plated on a germination medium and placed in an incubator at 16 to 22° C. The germination medium was prepared by adding 20 g/L of sucrose to MS The regeneration-inducing medium was prepared by adding benzyladenine (BA), 1-naphthaleneacetic acid (NAA), Augmentin, hygromycin, and sucrose at the respective concentrations indicated in Table 3 to MS medium and adjusting the pH of the medium to 5.8, followed by addition of 3 g/L of Gelrite, sterilization in an autoclave (at 121° C. for 20 minutes), and then cooling in a clean bench.

[Healthy Shoot Ratio]

In Reference Examples (Ref. Ex.) 21 and 22 and Comparative Reference Example (Comp. Ref. Ex.) 23, the number of healthy shoots which were not vitrified and were in a state suitable for rooting, and the number of vitrified shoots were counted to determine healthy shoot ratio. Table 3 shows the results.

Healthy shoot ratio (%)=[Number (count) of healthy shoots]/[Total number (count) of tested shoots]×100

TABLE 3

|  |  | Ref Ex. 21 | Ref Ex. 22 | Comp. Ref Ex. 23 |
|---|---|---|---|---|
| Regeneration-inducing medium | MS medium | MS medium | MS medium | MS medium |
|  | Benzyladenine (BA) [mg/L] | 0.5 | 1.0 | 0 |
|  | 1-Naphthaleneacetic acid (NAA)[mg/L] | 0.1 | 0.1 | 0 |
|  | Augmentin [mg/L] | 375 | 375 | 375 |
|  | Hygromycin [mg/L] | 0.5 | 0.5 | 0.5 |
|  | Sucrose [g/L] | 30 | 30 | 30 |
|  | Gelrite [g/L] | 3 | 3 | 3 |
| Total number (count) of tested shoots |  | 81 | 72 | 5 |
| Average number (count) of shoots per piece of callus |  | 3.1 | 2.9 | 2.5 |
| Number (count) of healthy shoots |  | 63 | 35 | 1 |
| Number (count) of vitrified shoots |  | 18 | 37 | 4 |
| Healthy shoot ratio (%) |  | 78 | 49 | 20 |

SEQUENCE LISTING FREE TEXT

SEQ ID NO: 1: Primer 1
SEQ ID NO: 2: Primer 2

The invention claimed is:

1. A method of producing a transgenic *Taraxacum* plant, comprising:

an infection step of infecting a tissue fragment from a *Taraxacum* plant with an *Agrobacterium tumefaciens* containing a plasmid containing a target gene or a fragment thereof and a hygromycin-resistance gene;

a selective culture step of selecting the tissue fragment that has acquired the target gene from the tissue fragment obtained in the infection step by using hygromycin;

a callus-inducing step of culturing the tissue fragment obtained in the selective culture step in a callus-inducing medium containing a cytokinin plant hormone, an auxin plant hormone, and a carbon source to form callus;

a regeneration-inducing step of culturing the callus obtained in the callus-inducing step in a regeneration-inducing medium containing a plant growth hormone and a carbon source to form an adventitious embryo, an adventitious bud, and a shoot; and a rooting step of culturing the shoot obtained in the regeneration-inducing step in a rooting medium to root the shoot, wherein the selective culture step comprises culturing the tissue fragment obtained in the infection step in a selective culture medium containing 0.1 to 2 mg/L of the hygromycin to select the tissue fragment that has acquired the target gene.

2. The method of producing a transgenic *Taraxacum* plant according to claim 1, wherein the callus-inducing medium contains the cytokinin plant hormone at a concentration of 0.5 to 1.2 mg/L and the auxin plant hormone at a concentration of lower than 1.2 mg/L.

3. The method of producing a transgenic *Taraxacum* plant according to claim 1, wherein the plant growth hormone in the regeneration-inducing medium comprises a cytokinin plant hormone at a concentration of 0.4 to 1.1 mg/L and an auxin plant hormone at a concentration of lower than 0.2 mg/L.

4. The method of producing a transgenic *Taraxacum* plant according to claim 1, wherein the *Taraxacum* plant is *Taraxacum kok-saghyz* or *Taraxacum brevicorniculatum*.

5. The method of claim 1, wherein the cytokinin plant hormone is benzyladenine and the auxin plant hormone is 1-naphthaleneacetic acid.

6. The method of claim 5, wherein the benzyladenine is at concentration of 0.8 to 6.0 mg/L, and the 1-naphthaleneacetic acid is at concentration of 0.1 to 1.0 mg/L.

7. The method of claim 1, wherein the benzyladenine is at concentration of 0.5 to 1.0 mg/L, and the 1-naphthaleneacetic acid is at concentration of 0.1 to 1.0 mg/L.

* * * * *